United States Patent
Mayer et al.

(10) Patent No.: US 6,231,348 B1
(45) Date of Patent: May 15, 2001

(54) HIGH TEMPERATURE STABILITY SENSOR CONTACT, METHOD FOR THE PRODUCTION THEREOF

(75) Inventors: Rolf Mayer, Winnenden; Theodor Graser, Stuttgart; Johann Wehrmann, Stuttgart; Heinz Eisenschmid, Stuttgart, all of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/077,070

(22) PCT Filed: Jun. 9, 1997

(86) PCT No.: PCT/DE97/01216

§ 371 Date: Nov. 5, 1998

§ 102(e) Date: Nov. 5, 1998

(87) PCT Pub. No.: WO98/12549

PCT Pub. Date: Mar. 26, 1998

(30) Foreign Application Priority Data

Sep. 19, 1996 (DE) .............................................. 196 38 208

(51) Int. Cl.[7] .................................................. H01R 41/00
(52) U.S. Cl. .............................................. 439/33; 204/424
(58) Field of Search ................................. 439/886, 885, 439/33, 874, 891; 204/424

(56) References Cited

U.S. PATENT DOCUMENTS

| | | | |
|---|---|---|---|
| 3,973,996 | * 8/1976 | Kennedy | 136/206 |
| 4,096,983 | 6/1978 | Beilein et al. | 228/122.1 |
| 4,138,604 | * 2/1979 | Harmsen et al. | 200/267 |
| 4,204,085 | * 5/1980 | Chapman et al. | 439/33 |
| 4,328,295 | * 5/1982 | Tanaka et al. | 204/424 |
| 4,465,742 | * 8/1984 | Nagashima et al. | 439/886 |
| 4,582,373 | * 4/1986 | Harmon | 439/33 |
| 4,689,810 | * 8/1987 | Devine, Jr. | 378/144 |
| 4,784,313 | * 11/1988 | Godziemba-Maliszewsk | 228/194 |
| 5,060,372 | * 10/1991 | Capp et al. | 439/885 |
| 5,098,548 | * 3/1992 | Duce | 204/424 |
| 5,110,034 | * 5/1992 | Simmonds | 228/179 |
| 5,361,971 | * 11/1994 | Williams et al. | 228/193 |
| 5,571,034 | * 11/1996 | Seidler | 439/885 |
| 6,055,847 | * 5/2000 | Hafele et al. | 204/424 |

FOREIGN PATENT DOCUMENTS 89 13 803    4/1990   (DE) .

* cited by examiner

Primary Examiner—Tulsidas Patel
Assistant Examiner—Hae Moon Hyeon
(74) Attorney, Agent, or Firm—Kenyon & Kenyon

(57) ABSTRACT

Multiple contacts are provided in an electrical contacting arrangement of a sensor element, and the sensor element has a connection-side section with contact points, or contact pads, which are each integrally bonded to a corresponding contact. Each of the multiple contacts, at least on the section in contact with the contact point on the sensor element, has a layer by which the integral bond is formed between the contact and the contact point on the sensor element. The contacts are joined to the corresponding contact points on the sensor element by diffusion soldering or diffusion welding. Each contact has a curved intermediate section which compensates for thermal and/or mechanical expansion and movements.

10 Claims, 4 Drawing Sheets

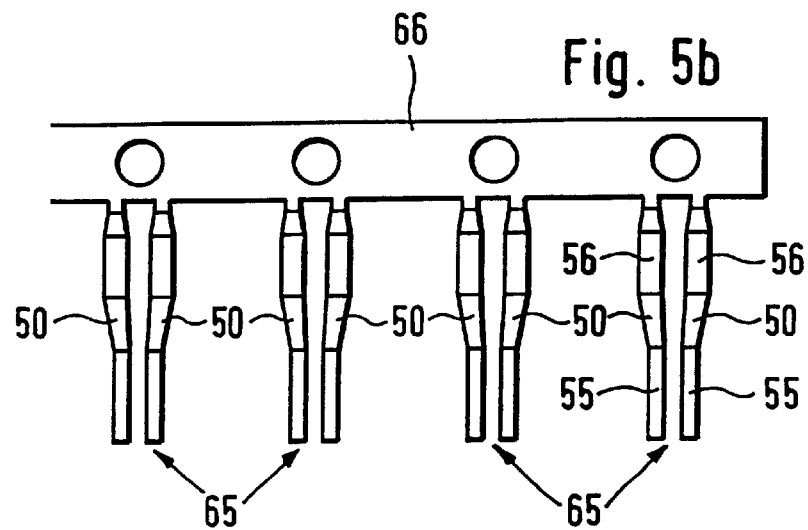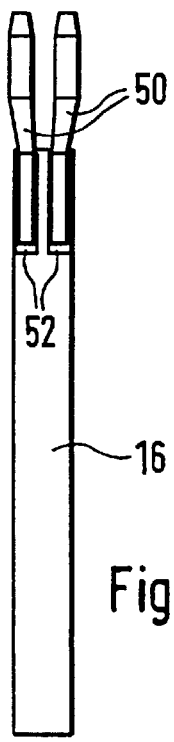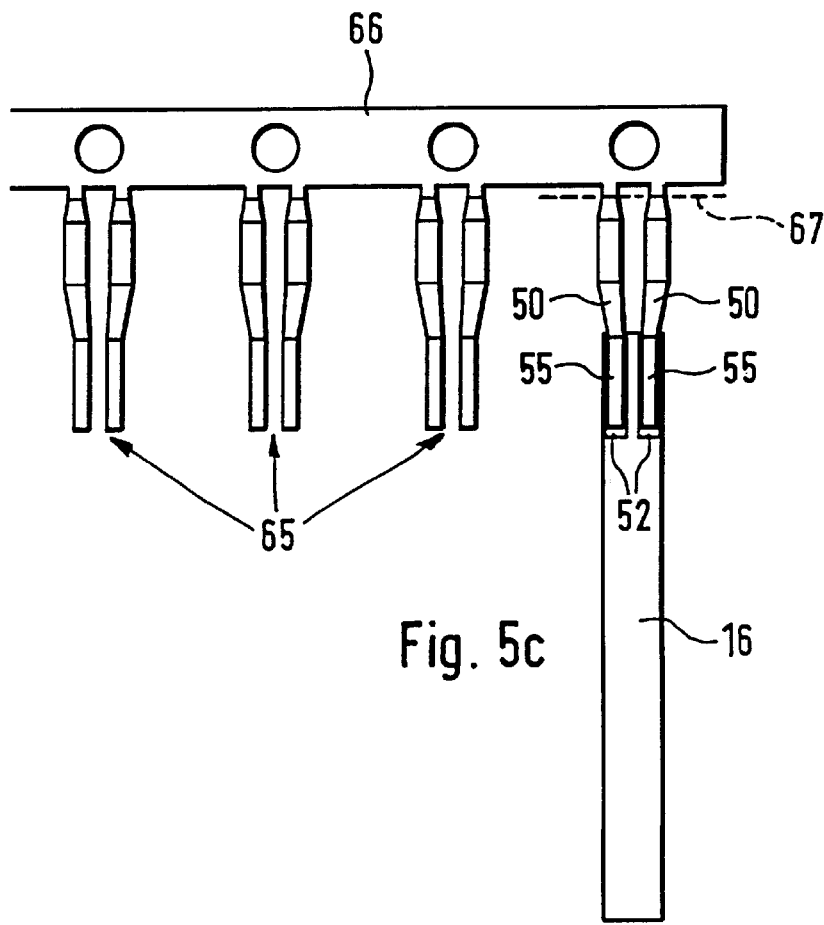

HIGH TEMPERATURE STABILITY SENSOR CONTACT, METHOD FOR THE PRODUCTION THEREOF

FIELD OF THE INVENTION

The present invention relates to an electrical contacting of a sensor element and, a method for its manufacture.

BACKGROUND INFORMATION

Planar sensor elements for determining the oxygen content in exhaust gas from internal combustion engines need a contacting at the surface to enable the sensor signal to be tapped off, and for provision with a heater voltage. Because the sensor element is used in exhaust systems of internal combustion engines, the contactings are subject to temperatures up to about 700° C. The contactings must ensure a reliable electrical and mechanical connection in this high-temperature range, and must permit simple and reliable handling during production.

International Patent Publication No. WO 95/18965, describes an electrical contacting of a sensor element of a gas sensor, in which contacts are integrally bonded by laser welding to the connection contacts of the sensor element. In so doing, the bare, metallic contact is welded onto the connection contact.

SUMMARY OF THE INVENTION

The present invention has the advantage that a reliable electrical mechanical connection is able to be produced which withstands temperature ranges of at least 700° C. The contacting is easily manipulable from a standpoint of production engineering.

Particularly easy handling of the contacts from a standpoint of production engineering is possible if the contacts are belted during the soldering or welding to the connection contacts, i.e. the individual contacts are interconnected by a metallic tape, and are separated from the metallic tape after the soldering or welding. A particularly reliable bond is produced by diffusion welding or diffusion soldering.

BRIEF DESCRIPTION OF THE DRAWINGS

FIG. 5a shows a step of a manufacturing sequence, from a standpoint of production engineering, of the contacting according to FIGS. 2 and 3.

FIG. 5b shows another step of the manufacturing sequence of the contacting according to FIGS. 2 and 3.

FIG. 5c shows yet another step of the manufacturing sequence of the contacting according to FIGS. 2 and 3.

FIG. 5d shows a further step of the manufacturing sequence of the contacting according to FIGS. 2 and 3.

DETAILED DESCRIPTION OF THE INVENTION

Figure 1:
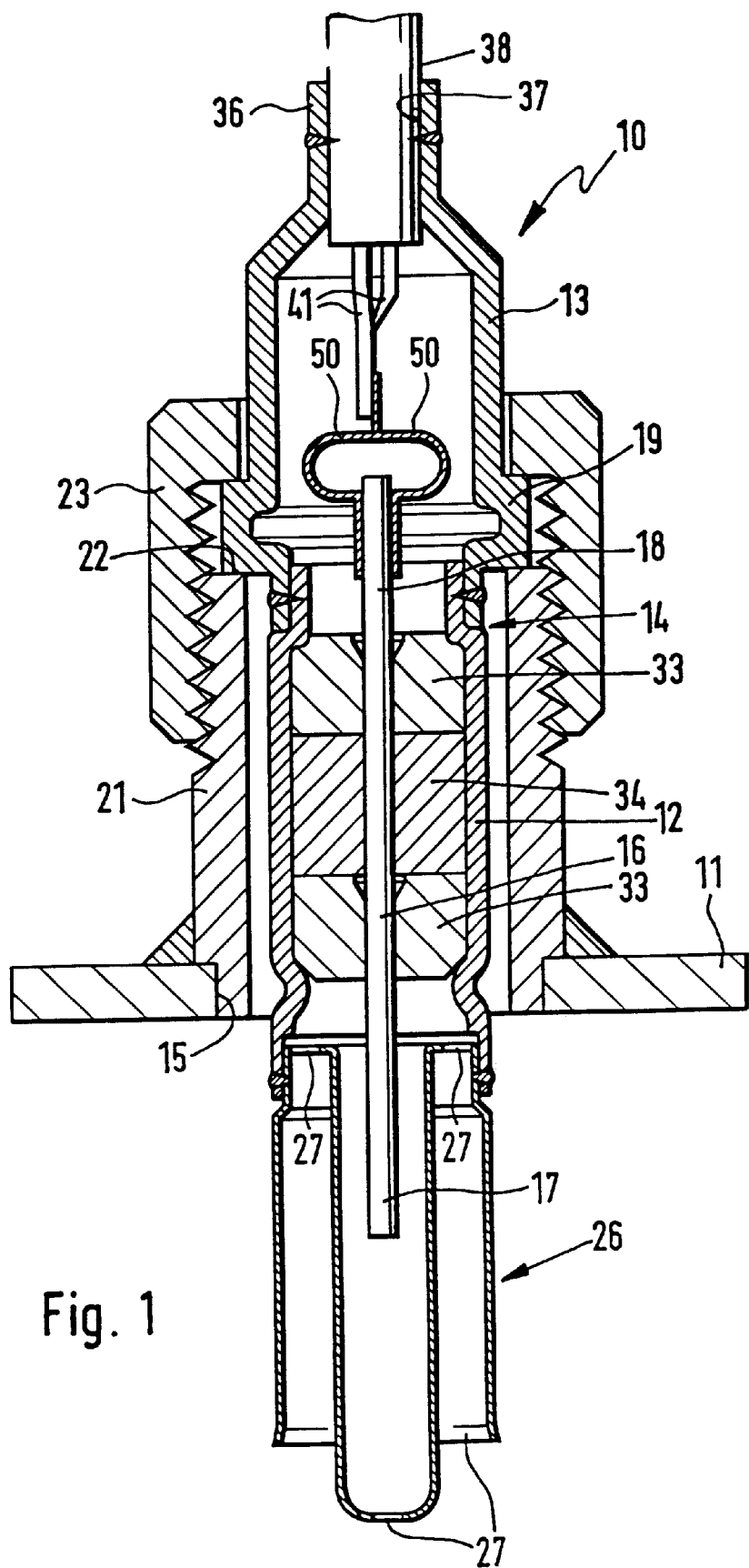
FIG. 1 shows a section through a gas sensor.

An electrochemical oxygen sensor 10 is mounted in an exhaust pipe 11, and has a metallic housing part 12 on the measuring-gas side and a metallic housing part 13 on the connection side, the two housing parts together forming a housing 14. Arranged in housing 14 is a planar sensor element 16 having a section 17 on the measuring-gas side and a section 18 on the connection side. Housing part 12 on the measuring-gas side is, for example, a tubular element that is open on both sides, in which two ceramic molded parts 33 and a sealing element 34, made e.g. of steatite powder, retain sensor element 16 in a gas-tight manner. Sensor element 16 is surrounded on the measuring-gas side by a double-walled protective tube 26 having gas orifices 27 for the ingress and/or emergence of gas.

Connection-side housing part 13 is likewise tubular, and has a sealing flange 19. At the end near the measuring gas, connection-side housing part 13 is welded in a gas-tight manner by a continuous welded seam to housing part 12 on the measuring-gas side. At the opposite end removed from the measuring gas, a tapering section 36 having an opening 37 is designed on housing part 13. A metallic, enclosing tube 38, for example, is welded into opening 37. Connecting cables 40, each having an electrical conductor 41 and a conductor insulation 42, are run in enclosing tube 38. Conductors 41 of conducting cables 40 are connected to contacts 50 (FIG. 2).

The exhaust pipe 11 has an opening 15, into which a cylindrical connecting piece 21 is welded in a gas-tight manner. Connecting piece 21 has an annular surface 22, upon which sealing flange 19 rests. Screwed onto connecting piece 21 is a screw cap 23 which acts on sealing flange 19 and presses it onto annular surface 22 of connecting piece 21.

Figure 2:
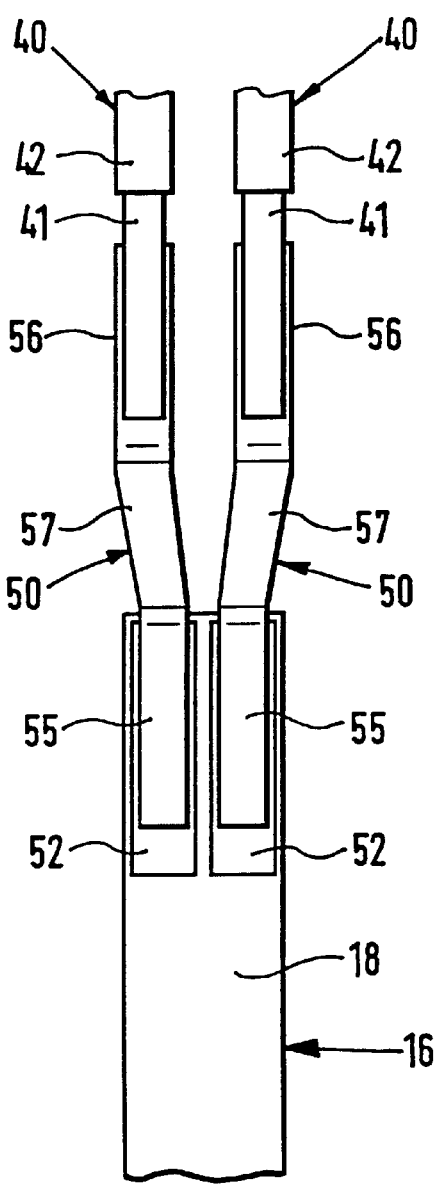
FIG. 2 shows a top view of a contacting of a sensor element of a first exemplary embodiment according to the present invention.
Figure 3:
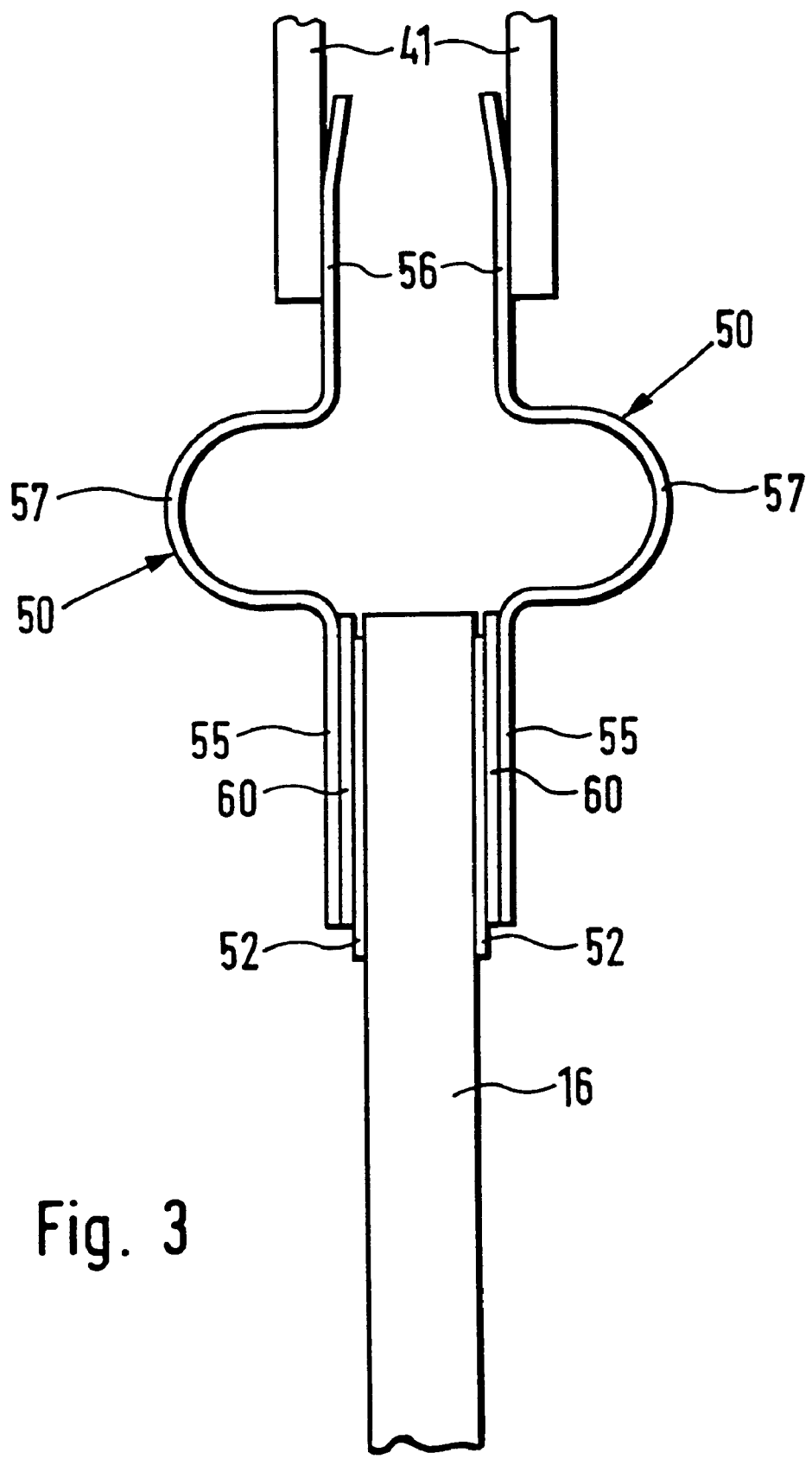
FIG. 3 shows an enlarged side view of the contacting according to FIG. 2.

A first exemplary embodiment of contacts 50 is shown in FIGS. 2 and 3. On connection-side section 18, sensor element 16 has contact points 52, formed on the surface, for electrodes (not shown) integrated into sensor element 16, and for a resistance heater (not shown) and likewise integrated into sensor element 16. Contact points 52 are made, for example, of a sintered platinum-cermet having at least 95% platinum. In the present exemplary embodiment according to FIGS. 2 and 3, there are four contact points 52, two contact points 52 being located on each side of sensor element 16.

The four contact points 52 are contacted in each case to a contact 50. Contacts 50 each have a section 55 on the sensor-element side, and a section 56 on the connection side, as well as a curved intermediate piece 57 arranged in between. Electrical conductors 41 of connecting cables 40 are welded to connection-side section 56. Curved intermediate piece 57 is used to compensate for thermal and/or mechanical expansions and movements. Contacts 50 are made e.g. of nickel or a nickel alloy.

In the exemplary embodiment according to FIGS. 2 and 3, sections 56 on the connection side are positioned corresponding to the arrangement of sections 55 on the sensor-element side, in each case two connection-side sections 56 lying opposite each other.

According to FIG. 3, contacts 50 in each case have a coating 60, at least on the surface joined to contact point 52. Depending on the bonding method used, coating 60 is made of silver, gold, copper or palladium, or of an alloy of these metals, or of a palladium-nickel alloy. The thickness of coating 60 is 1 to 50 $\mu$m. In the present exemplary embodiment, coating 60 is made of gold and is electrodeposited, the coating layer being 1 to 2 $\mu$m.

Figure 4:
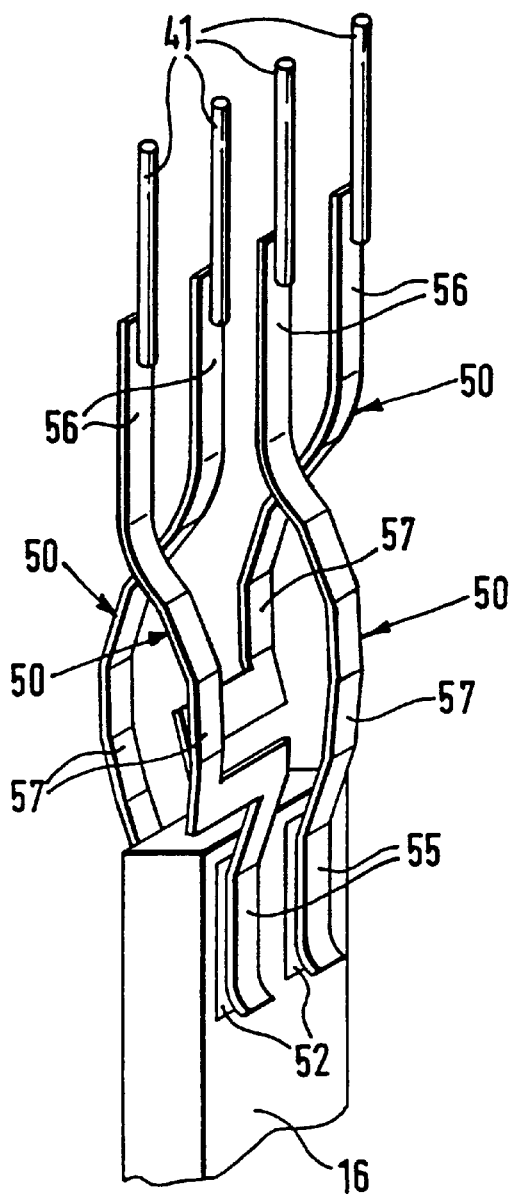
FIG. 4 shows a perspective representation of a contacting of a sensor element of a second exemplary embodiment according to the present invention.

A second exemplary embodiment for implementing contacts 50 is shown by FIG. 4. Here as well, two oppositely lying contacts 50 are contacted in each case to contact points 52 of sensor element 16. In contrast to the exemplary embodiment according to FIG. 2, here the connection-side sections 56 lie in alignment, side by side. The arrangement of contacts 50 according to FIG. 4 is so selected, that the positive terminal of the electrode and the positive terminal of the heating element do not lie beside one another.

The integral bond is produced expediently by diffusion welding or diffusion soldering. However, it is also conceivable to produce the integral bond by hard soldering, layer 60 being a temperature-resistant solder that is applied, for example, by plating.

FIGS. 5a to 5d show the sequence for producing the contacting from a standpoint of production engineering. FIG. 5a shows sensor element 16 with contact points 52 arranged on connection-side section 18. Provision is made on the opposite side of sensor element 16 for two further contact points which, however, are not visible in the drawing. According to FIG. 5b, contacts 50 are combined to form contact pairs 65 and are joined by a metallic tape 66, thus permitting a belted feed of contacts 50 to the jointing location. According to FIG. 5c, sections 55, on the sensor-element side, of a contact pair 65 are brought onto contact points 52 of sensor element 16. In this position, contacts 50 are integrally joined to contact points 52. After terminating the welding or soldering operation, contact pair 65 is separated from metallic tape 66 at a separation point 67. Initially, sensor element 16 is only contacted on one side to contacts 50 by this manufacturing sequence described above. Contact points 52 of the opposite side of sensor element 16 are subsequently joined in the same manner to contacts 50.

Another possibility for implementing the contacting from a standpoint of production engineering is that contacts 50 are joined together in the preassembled state, and are shaped to form at least one mutually opposing contact pair, in such a way that contacts 50 are capable of receiving the sensor element with prestressing. Contacts 50 thus pre-fabricated are slipped onto sensor element 16, contacts 50 being pressed onto contact points 52 because of the spring action. In this manner, it becomes possible to locate contacts 50 in position on sensor element 16 for the jointing process to be performed.

Sensor element 16, bonded to contacts 50, is finally inserted into housing part 12 on the measuring-gas side and, in the state thus built up, is contacted to the connecting cables.

What is claimed is:

1. An electrical contacting arrangement of a sensor element comprising:
   a single bonding layer;
   a contacts;
   wherein the single bonding layer is arranged at a section of the contact; and
   a contact point integrally bonded to the contact at the section, the contact point being located on the sensor element;
   wherein the single bonding layer provides an integral bond between the contact and the contact point.

2. The electrical contacting arrangement according to claim 1, wherein the contact includes a contacting section situated on a sensor-element side of the contact, a connection section situated on a connection side of the contact, and a curved intermediate piece positioned between the contacting section and the connection section, and wherein the contacting section is positioned at least partially flat on the contact point.

3. The electrical contacting arrangement according to claim 1, further comprising additional plurality of contacts all of the contacts being interconnected in a preassembled state by a metallic tape, and wherein a separation point is positioned between the metallic tape and the plurality of contacts.

4. The electrical contacting arrangement according to claim 1, further comprising additional plurality of contacts all of the contacts being interconnected in a preassembled state and shaped to form at least one mutually opposing contact pair so that the sensor element clamps between the contacts of the at least one mutually opposing contact pair as a function of a spring action of the at least one mutually opposing contact pair.

5. The electrical contacting arrangement according to claim 1, wherein the single bonding layer is composed of one of:
   a silver material, a gold material, a copper material and a palladium material;
   an alloy composed of at least two of the silver material, the gold material, the copper material and the palladium material; and
   a palladium-nickel alloy.

6. The electrical contacting arrangement according to claim 1, wherein a thickness of the layer is between 1 $\mu$m and 50 $\mu$m.

7. The electrical contacting arrangement according to claim 6, wherein the thickness is between 2 $\mu$m and 50 $\mu$m.

8. The electrical contacting arrangement according to claim 1, wherein the contact point is composed of a cermet material, and wherein after a sintering procedure, the cermet material is composed of at least 95% platinum material by weight.

9. A method for producing an electrical contacting arrangement comprising the steps of:
   providing a single diffusion-active layer;
   wherein the single diffusion active layer is provided at a contact; and
   joining the contact to a contact point of a sensor element by one of a diffusion soldering procedure and a diffusion welding procedure.

10. The method according to claim 9, wherein a plurality of contacts are provided,. and further comprising the steps of:
   joining the plurality of contacts using a metallic tape so that the plurality of contacts are fed in a belted state to the contact point; and
   thereafter, separating the plurality of contacts from the metallic tape.

* * * * *